(12) United States Patent  
Hanebuchi

(10) Patent No.: US 7,275,825 B2  
(45) Date of Patent: Oct. 2, 2007

(54) EYE REFRACTIVE POWER MEASUREMENT APPARATUS

(75) Inventor: Masaaki Hanebuchi, Nukata-gun (JP)

(73) Assignee: Nidek Co., Ltd., Gamagori (JP)

( * ) Notice: Subject to any disclaimer, the term of this patent is extended or adjusted under 35 U.S.C. 154(b) by 318 days.

(21) Appl. No.: 11/140,734

(22) Filed: Jun. 1, 2005

(65) Prior Publication Data

US 2005/0270488 A1    Dec. 8, 2005

(30) Foreign Application Priority Data

Jun. 2, 2004    (JP)    ............ 2004-164335

(51) Int. Cl.  
*A61B 3/14* (2006.01)

(52) U.S. Cl. .............. 351/206; 351/212; 351/214

(58) Field of Classification Search ........ 351/205–207, 351/210–212, 214, 221; 396/18; 600/558  
See application file for complete search history.

(56) References Cited

U.S. PATENT DOCUMENTS 5,523,809 A * 6/1996 Kohayakawa ............ 351/211  
2005/0068497 A1   3/2005 Hanebuchi et al.

FOREIGN PATENT DOCUMENTS

| JP | A 01-129830 | 5/1989 |
| JP | A 01-293841 | 11/1989 |
| JP | A 05-031075 | 2/1993 |
| JP | A 08-103413 | 4/1996 |
| JP | A 11-225963 | 8/1999 |
| JP | A 2002-336200 | 11/2002 |

* cited by examiner

*Primary Examiner*—Hung Dang  
*Assistant Examiner*—Joseph Martinez  
(74) *Attorney, Agent, or Firm*—Oliff & Berridge, PLC

(57) ABSTRACT

An eye refractive power measurement apparatus capable of reducing an influence of scattered light and performing measurement with high accuracy. The apparatus has a measurement optical system including a system having a light source projecting spot-shaped measurement light onto a fundus of an examinee's eye, and a system having an optical axis, a photodetector, a ring-shaped aperture, a member by which the light reflected from the fundus via a peripheral pupillary portion and the aperture forms a ring-shaped image on the photodetector, and a diaphragm of a size such that a projection region by the diaphragm on the photodetector overlaps the axis within a predetermined amount and that the reflection light forms the image within the region in projecting the measurement light onto a myopic eye with the measurable highest diopter, and a part which obtains the eye refractive power based on an output from the photodetector.

4 Claims, 4 Drawing Sheets

EYE REFRACTIVE POWER MEASUREMENT APPARATUS

BACKGROUND OF THE INVENTION

1. Field of the Invention

The present invention relates to an eye refractive power measurement apparatus for measuring eye refractive power of an eye of an examinee objectively.

2. Description of Related Art

Conventionally, there is an eye refractive power measurement apparatus which projects spot-shaped measurement light onto a fundus via a central pupillary portion and photo-receives the light reflected from the fundus via a peripheral pupillary portion and a ring-shaped aperture (opening) which is arranged at an optically conjugate position with a pupil using a two-dimensional photodetector or the like to obtain eye refractive power based on a photo-receiving result thereof.

In the conventional apparatus, however, there is a case where scattered light generated due to a crystalline lens, a cornea and the like has an influence on measurement. Especially in the case of measuring a myopic eye with a high diopter, the scattered light exerts greater influence since it is collected into the center part of a photo-receiving surface of the photodetector.

SUMMARY OF THE INVENTION

An object of the invention is to overcome the problems described above and to provide an eye refractive power measurement apparatus capable of reducing an influence of scattered light and performing measurement with high accuracy.

To achieve the objects and in accordance with the purpose of the present invention, an eye refractive power measurement apparatus for measuring eye refractive power of an eye of an examinee has a measurement optical system including a projection optical system having a light source which projects spot-shaped measurement light onto a fundus of the eye and a photo-receiving optical system having an optical axis, a photodetector arranged on the optical axis, a ring-shaped aperture having the optical axis as its center which is arranged at a position conjugate with a pupil of the eye and passes the light reflected from the fundus via a peripheral papillary portion of the eye, an image-forming optical member arranged on the optical axis by which the reflection light from the fundus via the peripheral pupillary portion and the ring-shaped aperture forms a ring-shaped image on the photodetector, and a diaphragm having the optical axis as its center which is arranged at a position conjugate with the fundus and on a side of the eye relative to the image-forming optical member, and a calculation part which obtains the eye refractive power based on an output from the photodetector, wherein the diaphragm is set to have a size such that a projection region by the diaphragm through the image-forming optical member on the photodetector overlaps the optical axis only within a predetermined amount and such that the reflection light forms the image within the projection region by the diaphragm in projecting the measurement light onto a myopic eye with the measurable highest diopter.

In another aspect of the invention, an eye refractive power measurement apparatus for measuring eye refractive power of an eye of an examinee has a measurement optical system including a projection optical system having a light source which projects spot-shaped measurement light onto a fundus of the eye and a photo-receiving optical system having an optical axis, a photodetector arranged on the optical axis, at least three apertures arranged at positions conjugate with a pupil of the eye which are provided in at least three meridian directions on the same circumference having the optical axis as its center and passes the light reflected from the fundus via a peripheral pupillary portion of the eye, an image-forming optical member arranged on the optical axis by which the reflection light from the fundus via the peripheral pupillary portion and the respective apertures is deflected in directions away from the optical axis and forms dot-shaped images on the photodetector and a diaphragm having the optical axis as its center which is arranged at a position conjugate with the fundus and on a side of the eye relative to the image-forming optical member, and a calculation part which obtains the eye refractive power based on an output from the photodetector, wherein the diaphragm is set to have a size such that projection regions by the diaphragm through the image-forming optical member on the photodetector are prevented from overlapping each other and such that the reflection light forms the images within the projection regions by the diaphragm in projecting the measurement light onto a myopic eye with the measurable highest diopter.

Additional objects and advantages of the invention are set forth in the description which follows, are obvious from the description, or may be learned by practicing the invention. The objects and advantages of the invention may be realized and attained by the eye refractive power measurement apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
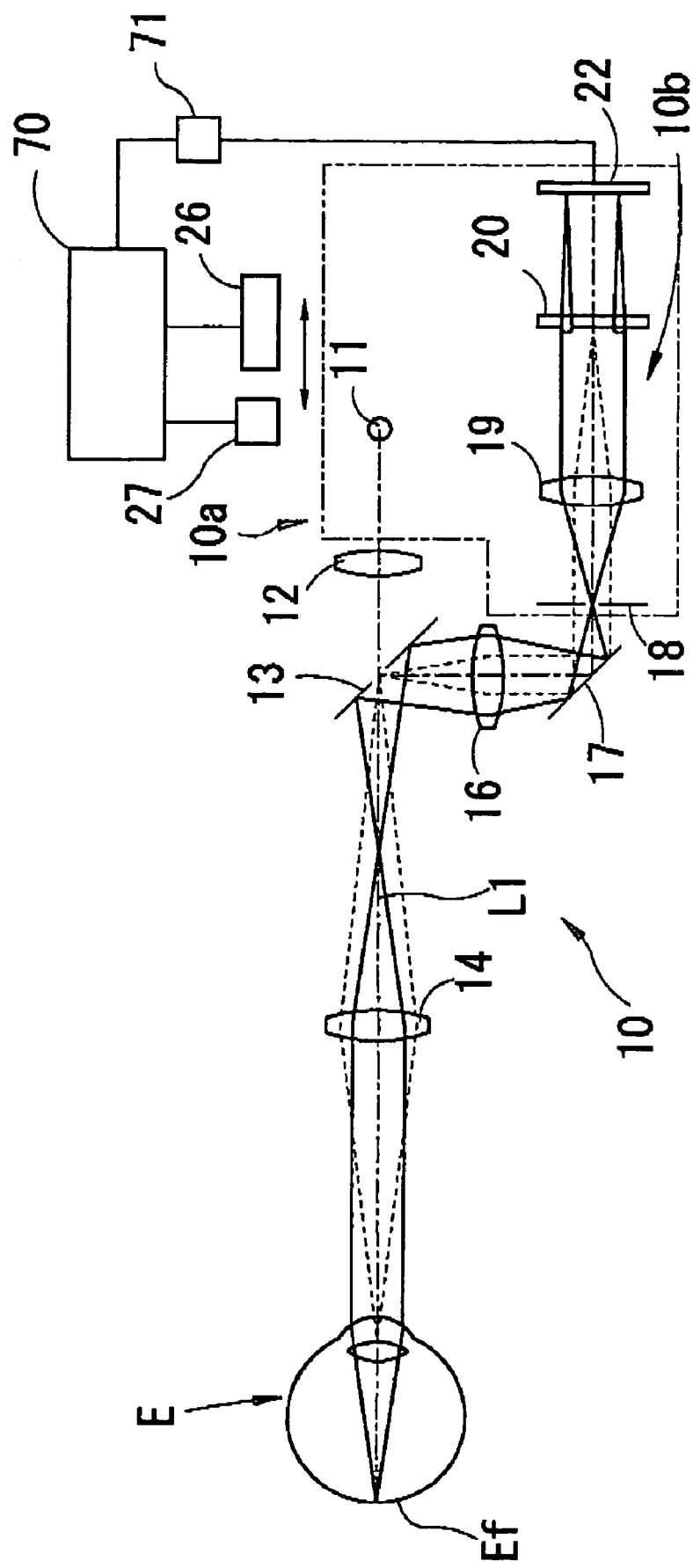
FIG. 1 is a view showing a schematic configuration of an optical system and a control system in an eye refractive power measurement apparatus consistent with one embodiment of the present invention.

A detailed description of one preferred embodiment of an eye refractive power measurement apparatus embodied by the present invention is provided below with reference to the accompanying drawings. FIG. 1 is a view showing a schematic configuration of an optical system and a control system in the eye refractive power measurement apparatus consistent with one embodiment of the present invention.

A measurement optical system 10 is constituted of a projection optical system 10a for projecting spot-shaped measurement light onto a fundus Ef via a central pupillary portion of an eye E of an examinee, and a photo-receiving optical system 10b for photo-receiving the light reflected from the fundus Ef via a peripheral pupillary portion of the eye E. The projection optical system 10a includes an infrared point light source 11 such as an LED and an SLD, a relay lens 12, a hole mirror 13, and an objective lens 14 for measurement which are arranged on a measurement optical axis L1. The light source 11 is arranged to have a positional relationship optically conjugate with the fundus Ef. In addition, a hole portion of the mirror 13 is arranged to have a positional relationship optically conjugate with a pupil of the eye E. Incidentally, the term "conjugate" referred to in the present specification represents that the positional relationship does not have to be strictly conjugate, but may be conjugate only with needed accuracy in relation to measurement accuracy.

The photo-receiving optical system 10b shares the lens 14 and the mirror 13 in the projection optical system 10a and includes a relay lens 16 and a reflection mirror 17 which are arranged on the optical axis L1 in a reflecting direction of the mirror 13, and a photo-receiving diaphragm 18, a collimator lens 19, a ring lens 20 and an image-pickup element 22 being a two-dimensional photodetector such as a CCD which are arranged on the optical axis L1 in a reflecting direction of the mirror 17. The diaphragm 18 is located at a front focal point of the lens 19, and the image-pickup element 22 is located at a back focal point of the lens 20. The diaphragm 18 and the image-pickup element 22 are arranged to have a positional relationship optically conjugate with the fundus Ef. An output from the image-pickup element 22 is inputted to a calculation control part 70 via an image processing part 71.

Figures 2A, 2B:
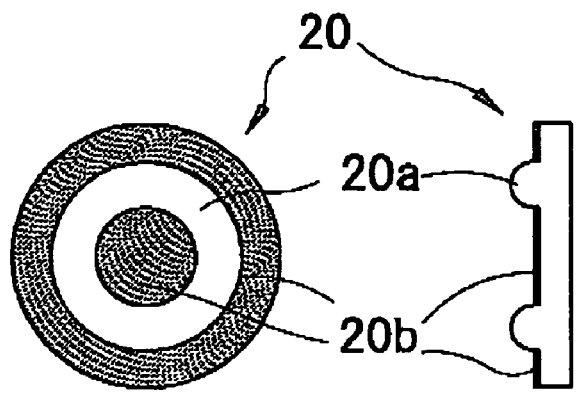
FIGS. 2A and 2B are views showing a schematic configuration of a ring lens.

As shown in FIGS. 2A and 2B, the ring lens 20 is constituted of a lens portion 20a where a cylindrical lens is formed in a ring shape on one side of a transparent plate, and a light shielding portion 20b formed by coating for light shielding which is provided to other portions than the ring-shaped cylindrical lens of the lens portion 20a. Owing to such constitution, a ring-shaped aperture (opening) is formed on the ring lens 20. Incidentally, since the ring lens 20 is arranged so that the formed ring-shaped aperture has a positional relationship optically conjugate with the pupil, the light reflected from the fundus Ef is, via the peripheral pupillary portion, picked up in a ring shape of a size corresponding to the formed ring-shaped aperture. When parallel light enters the ring lens 20, a ring image of the same size as the ring-shaped aperture is formed on the image-pickup element 22 arranged at the focal point of the ring lens 20. That is to say, the ring lens 20 separates the light reflected from the fundus Ef into a ring shape, and constitutes an image-forming member by which the ring image is formed on the image-pickup element 22 through its light-collecting action. Besides, in the ring lens 20, the ring portion 20a and the light shielding portion 20b may be constituted of separate members.

In addition, the light source 11 in the projection optical system 10a, and the diaphragm 18, the lens 19, the ring lens 20 and the image-pickup element 22 in the photo-receiving optical system 10b are preferably movable integrally in the optical axis L1 direction by a movement unit 26. A travel position (travel amount) of these components is detected by a potentiometer 27. Besides, regardless of movement of these components, the mirror 13 and the ring lens 20 are arranged to have a positional relationship optically conjugate with the pupil under a fixed magnification.

The measurement light from the light source 11 is projected onto the fundus Ef through the lens 12 to the lens 14 to form a point-light-source image in a spot shape on the fundus Ef. The light of the point-light-source image formed on the fundus Ef is reflected and scattered thereby to exit from the eye E. Then, the light is collected through the lens 14 and reflected by a periphery of the hole portion of the mirror 13 to be collected again on an aperture (opening) surface of the diaphragm 18 through the lens 16 and the mirror 17, and made into approximately parallel light by the lens 19 to be made into ring-shaped light by the ring lens 20, and then photo-received on the image-pickup element 22. In the projection optical system 10a, the measurement light which is thin is projected onto the fundus Ef via the central pupillary portion, and in the photo-receiving optical system 10b, the light reflected from the fundus Ef is photo-received (picked up) via the peripheral pupillary portion. The ring-shaped light photo-received (picked up) through the ring lens 20 is, for example, 2.0 mm in inside diameter and 2.8 mm in outside diameter on a pupillary surface.

Here, in a case where the eye E is emmetropia, the image-pickup element 22 and the fundus Ef become conjugate, and the light reflected from the fundus Ef enters the ring lens 20 as approximately parallel light; therefore, a ring image having the same size and shape as the ring-shaped aperture of the ring lens 20 is formed on the image-pickup element 22. On the other hand, in a case where the eye E has abnormality in a spherical refractive component, a ring image of a size corresponding to an error of the spherical refractive component is formed on the image-pickup element 22. Further, in a case where the eye E has abnormality in an astigmatic (cylindrical) refractive component, an oval ring image corresponding to an error of the astigmatic refractive component is formed on the image-pickup element 22. Accordingly, by analyzing the size and shape of the ring image formed on the image-pickup element 22, a refractive error in each meridian direction may be obtained, to which predetermined processing is provided to obtain values of S (spherical power), C (astigmatic (cylindrical) power) and A (an astigmatic (cylindrical) axial angle). Besides, the size and shape of the ring image may be obtained from an edge position of the ring image, the barycenter position or the peak position of the ring image in light intensity level, and the like.

Further, the light source 11, the diaphragm 18, and the image-pickup element 22 are arranged to have a positional relationship conjugate with the fundus Ef by integrally moving the light source 11, the diaphragm 18, the lens 19, the ring lens 20, and the image-pickup element 22 in the optical axis L1 direction while making the ring image on the image-pickup element 22 thinnest, brightest, or making an average size of the ring image same as the ring size of the ring lens 20. Then, the travel position (travel amount) detected by the potentiometer 27 is converted to the error of the spherical refractive component. As the sum of this error of the spherical refractive component and the refractive error in the each meridian direction obtained by the ring image on the image-pickup element 22, a refractive error of the eye E in each meridian direction may be obtained. With such constitution that the optical system from the diaphragm 18 to the image-pickup element 22 is moved to the position conjugate with the fundus Ef in accordance with the refractive error of the eye E as described above, measurement of a great refractive error may be supported while not scaling down resolution upon ring image analysis and not enlarging the size of a photo-receiving surface of the image-pickup element 22.

Figures 3A, 3B:
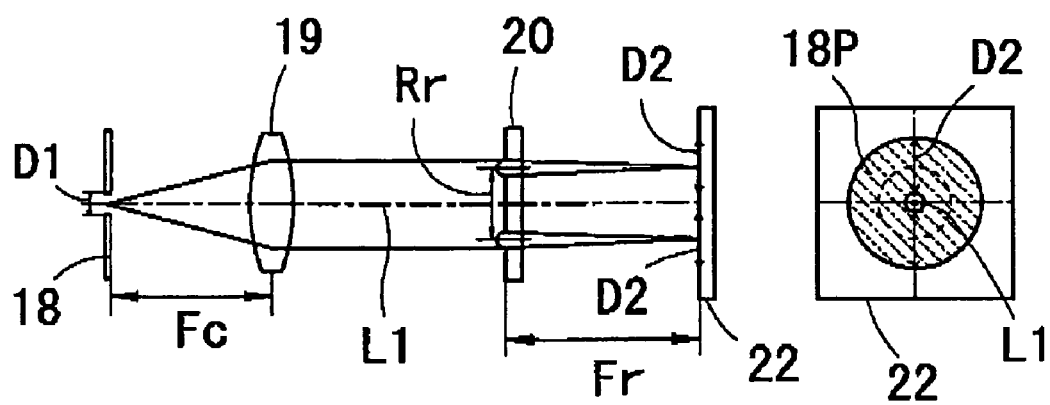
FIG. 3A is an enlarged view showing a part of a photo-receiving optical system.
FIG. 3B is a view showing a projection region by a photo-receiving diaphragm on an image-pickup element.

FIG. 3A is an enlarged view showing a part of the photo-receiving optical system 10b, and FIG. 3B is a view showing a projection region 18P by the diaphragm 18 on the image-pickup element 22. Besides, the projection region 18P by the diaphragm 18 indicates a region of a projection image of the diaphragm 18 formed on the image-pickup element 22 via the lens 19 and the ring lens 20 when the diaphragm 18 is illuminated uniformly from the side of the mirror 17.

In the present embodiment, a detection (photo-receiving) range on the image-pickup element 22 is made more than two times as large as a diameter Rr of the ring-shaped aperture of the ring lens 20. Here, let Fc represent a focal length of the lens 19 and Fr represent that of the ring lens 20, a projection magnification β of the diaphragm 18 is defined as:

$$\beta = -Fr/Fc.$$

Let D1 represent a diameter of the diaphragm 18 (an aperture (opening) size thereof) and D2 represent a size (width) of the projection region 18P by the diaphragm 18 on the image-pickup element 22, their relation is given by the following expression:

$$D2 = D1 \times |\beta|.$$

Here, the maximum size of the diameter D1 of the diaphragm 18 is designed to satisfy:

$$D2 \leq Rr,$$

more specifically, $$D1 \leq Rr/|\beta|,$$

and thereby, the projection image of the diaphragm 18, which is separated into a ring shape by the lens 19 and the ring lens 20 to be projected onto the image-pickup element 22, is prevented from overlapping a center part of the photo-receiving surface of the image-pickup element 22, and preferably, $$D1 = Rr/|\beta|,$$

by which the center part is made to exactly include the optical axis L1.

Figure 4:
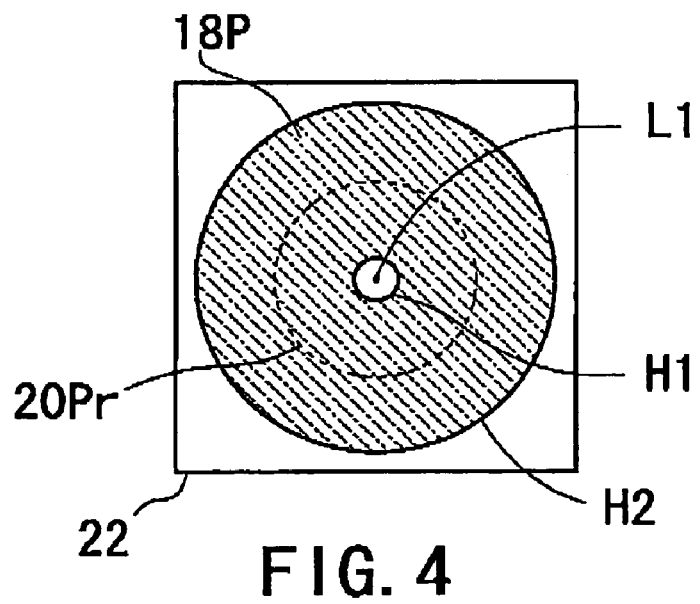
FIG. 4 is a view showing a relation between the projection region by the photo-receiving diaphragm on the image-pickup element and a ring image formed by light reflected from a fundus on the image-pickup element.

FIG. 4 is a view showing a relation between the projection region 18P by the diaphragm 18 on the image-pickup element 22 and the ring image formed by the light reflected from the fundus Ef on the image-pickup element 22. Reference numeral 20Pr denotes the peak position of the ring image in light intensity level. In a case where the diaphragm 18, the image-pickup element 22 and the like are not moved in the optical axis L1 direction, the ring image has a diameter proportional to the error of the spherical refractive component of the eye E.

The ring lens 20 is circular and only has refractive power in a meridian direction, so that the projection region 18P by the diaphragm 18 on the image-pickup element 22 is represented as a region surrounded by an inner envelope H1 and an outer envelope H2 having the optical axis L1 as their center. When the aperture size of the diaphragm 18 is made smaller, a diameter of the inner envelope H1 becomes larger and that of the outer envelope H2 becomes smaller.

Here, since the projection region 18P is the region of the projection image of the diaphragm 18 formed on the image-pickup element 22 when the diaphragm 18 is illuminated uniformly from the side of the mirror 17, the light passing through the diaphragm 18 may be present only within the region surrounded by the envelopes H1 and H2. Accordingly, the ring image formed by the light reflected from the fundus Ef, including a scattered component of the light, may be present only within the region surrounded by the envelopes H1 and H2.

Consequently, the minimum size of the diaphragm 18 is determined in relation to a measurable region for the error of the spherical refractive component of the eye E. In other words, the minimum size of the diaphragm 18 is determined so that the ring image (an image forming position of the light reflected from the fundus Ef) falls within the projection region 18P in measuring a myopic eye with the highest measurable diopter (e.g., an eye with −25.0 D) and also in measuring a hyperopic eye with the highest measurable diopter (e.g., an eye with +25.0 D).

Figure 5A:
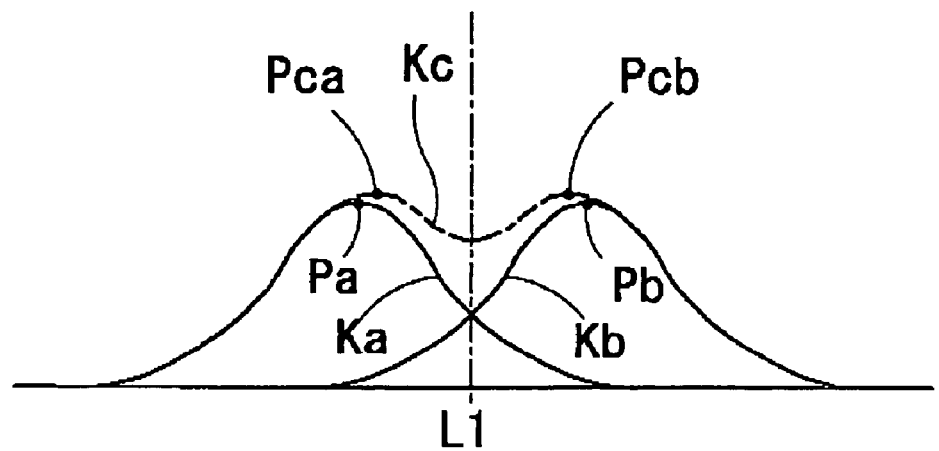
FIGS. 5A and 5B are views illustrating a function of the photo-receiving diaphragm.

Next, a function of the diaphragm 18 will be described referring to FIGS. 5A and 5B. FIG. 5A is a view showing a photo-receiving amount of the ring image detected in a horizontal meridian direction on the image-pickup element 22 in a case where the diaphragm 18 is not provided. Ka denotes distribution of light intensity of the ring image formed by the left half of the ring-shaped aperture, and Pa denotes a peak position thereof. Kb denotes distribution of light intensity of the ring image formed by the right half of the ring-shaped aperture, and Pb denotes a peak position thereof. The light intensity distribution Ka and Kb overlap each other over the optical axis L1. Light intensity distribution Kc denotes the sum of the light intensity distribution Ka and Kb. On the image-pickup element 22, the light intensity distribution Ka and Kb are detected as the light intensity distribution Kc while not being distinguished from each other. Pca and Pcb denote peak positions in the light intensity distribution Kc when dividing the light intensity distribution Kc by the optical axis L1. Here, if the peak position in the light intensity distribution is detected according to a common method for detecting the ring image position, the peak positions Pca and Pcb, which are different from the original (correct) peak positions Pa and Pb, are detected. Consequently, an error in a measurement result emerges. Besides, not in the case of detecting the peak position in the photo-receiving amount distribution, but in the case of detecting, for example, the intermediate position between two points beyond a predetermined threshold, a similar problem also occurs.

Figure 5B:
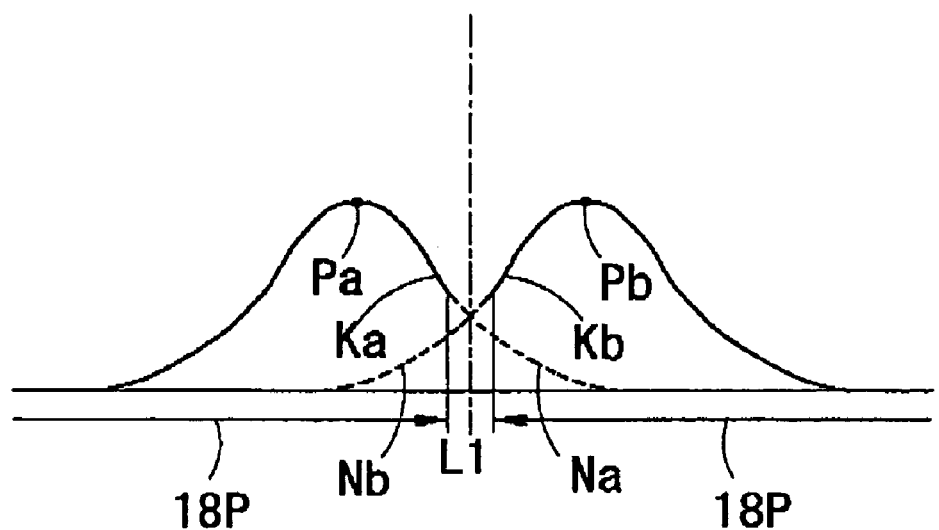

In contrast, FIG. 5B is a view showing a photo-receiving amount of the ring image detected in the horizontal meridian direction on the image-pickup element 22 in the case of providing the diaphragm 18 of the size determined as above. The diaphragm 18 cuts, in advance, scattered light in parts of the light intensity distribution Ka and Kb, which are beyond the inner envelope H1 (i.e., a part indicated by a dotted line Na in the distribution Ka, and a part indicated by a dotted line Nb in the distribution Kb), preventing the overlapping of the light reflected from the fundus Ef including the scattered light shown in FIG. 5A. Therefore, the original peak positions Pa and Pb may be detected, which eliminates a cause of emergence of the measurement error.

Incidentally, for expanding the measurable region, it is preferable only if the maximum size of the diameter D1 of the diaphragm 18 is made into such a size that allows D2=Rr while the projection region 18P may include the optical axis L1. As a matter of fact, even if the projection region 18P overlaps the optical axis L1 in some degree, it does not matter with regard to its use as long as light intensity in the overlap and the original peak positions Pa and Pb shown in FIG. 5B are respectively detected. This case is also included in the present invention.

Figure 6:
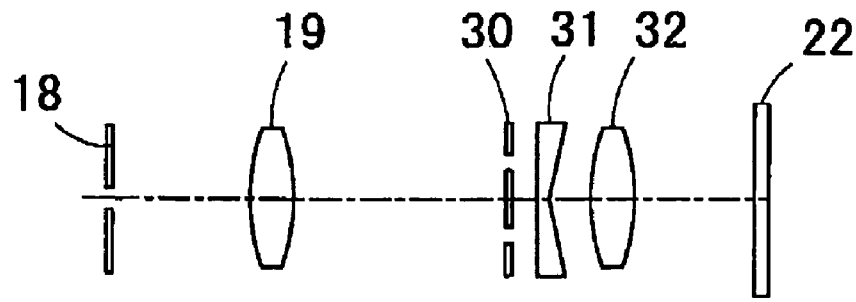
FIG. 6 is a view illustrating a modified embodiment of the photo-receiving optical system.

Various modifications may be applied to the above-described preferred embodiment. For example, instead of providing the ring lens 20 being the image-forming optical member between the lens 19 and the image-pickup element 22, it is possible to constitute a photo-receiving optical system shown in FIG. 6. In FIG. 6, arranged on an optical path between the diaphragm 18 and the image-pickup element 22 are the lens 19, an aperture member 30 which is arranged at a position conjugate with the pupil and provided with apertures (openings) placed in at least three meridian directions on the same circumference, light deflection prisms 31 which are arranged in correspondence with positions of the respective apertures, and an image-forming lens 32. The number of the apertures of the aperture member 30 is, for example, six, and the prisms 31 are wedge prisms corresponding to the six apertures. The light reflected from the fundus Ef passing through the six apertures is deflected by the respective prisms 31 in directions away from the optical axis L1, and forms six images in dotted shapes on the image-pickup element 22 by the image-forming lens 32.

Figure 7:
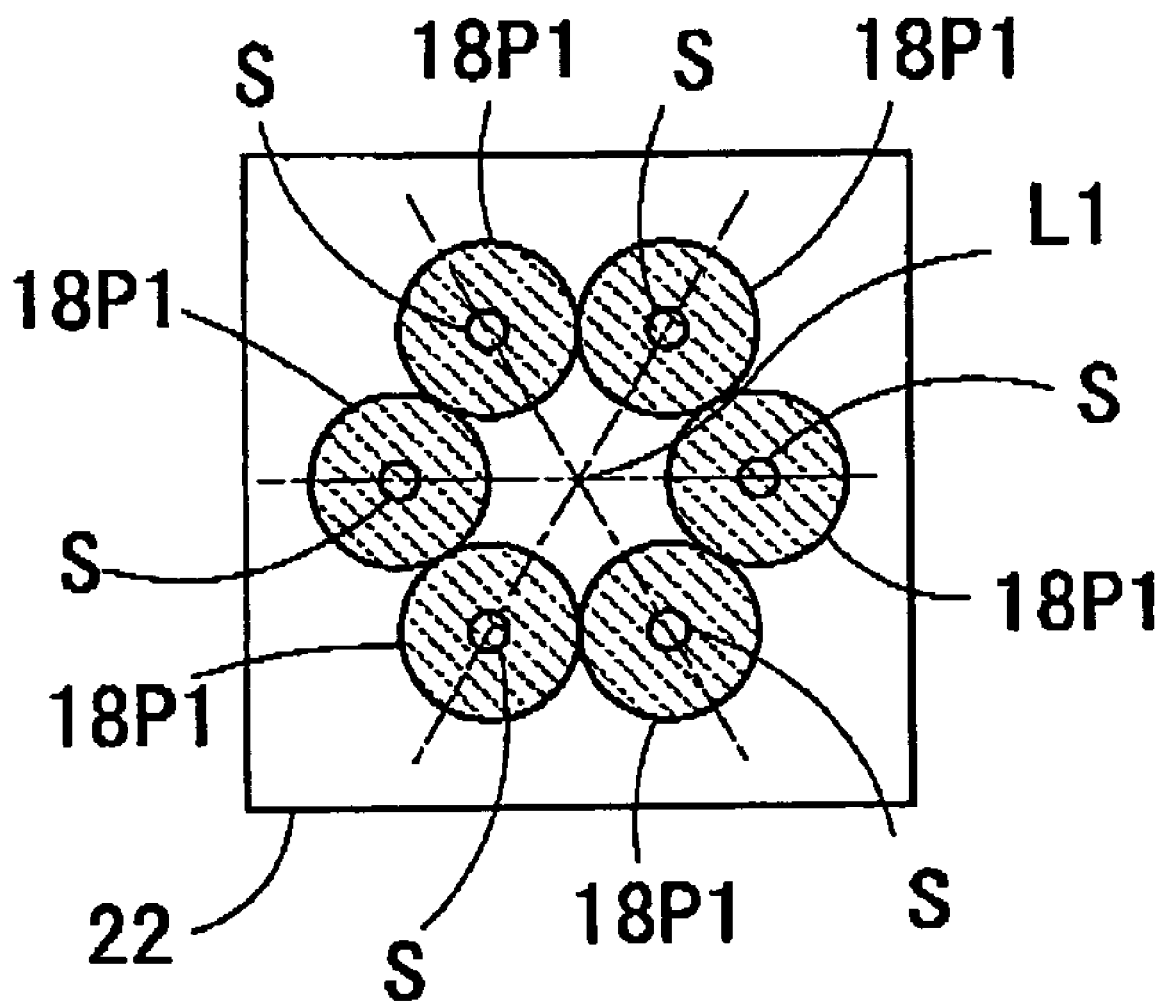
FIG. 7 is a view showing projection regions by the photo-receiving diaphragm on the image-pickup element.

In this photo-receiving optical system, a projection image of the diaphragm 18 is also projected in the respective directions away from the optical axis L1 by the image-forming optical members from the lens 19 to the lens 32. FIG. 7 is a view showing projection regions 18P1 by the diaphragm 18 on the image-pickup element 22. In the optical system, the aperture size of the diaphragm 18 is made so that the adjacent projection regions 18P1 do not overlap each other, allowing an influence of scattered light to be precluded, and images S in dotted shapes to be detected with high accuracy. Also in this case, the aperture size is made so that the images S are formed within the projection regions 18P1 in measuring a myopic eye with the highest measurable diopter and measuring a hyperopic eye with the highest measurable diopter. Similarly to the aforementioned embodiment, also by moving the photo-receiving optical system from the diaphragm 18 to the image-pickup element 22 and the light source 11 to a position conjugate with the fundus Ef in accordance with the eye refractive error, measurement of a great refractive error may be supported while not scaling down resolution upon the images S in detection.

Further, the above-described preferred embodiment may be modified to be embodied as follows. For example, a shape of the diaphragm 18 may be square, not circular. In addition, the diaphragm 18 may be arranged at a position conjugate with the fundus Ef which is between the lens 14 and the mirror 13, not in the position conjugate with the fundus Ef which is between the mirror 17 and the lens 19. In this case, if the measurement light from the light source 11 is made thin to be able to pass the diaphragm 18 sufficiently, it produces a similar effect without a loss in its light intensity. Such a modification is included in the present invention as far as its technical idea is the same as that of the preferred embodiment.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An eye refractive power measurement apparatus for measuring eye refractive power of an eye of an examinee, the apparatus comprising:
   a measurement optical system including
      a projection optical system having a light source, which projects spot-shaped measurement light onto a fundus of the eye, and
      a photo-receiving optical system having
         an optical axis,
         a photodetector arranged on the optical axis,
         a ring-shaped aperture having the optical axis as its center, which is arranged at a position conjugate with a pupil of the eye, and passes the light reflected from the fundus via a peripheral pupillary portion of the eye,
         an image-forming optical member arranged on the optical axis, by which the reflection light from the fundus via the peripheral pupillary portion and the ring-shaped aperture forms a ring-shaped image on the photodetector, and
         a diaphragm having the optical axis as its center, which is arranged at a position conjugate with the fundus and on a side of the eye relative to the image-forming optical member; and
   a calculation part which obtains the eye refractive power based on an output from the photodetector,
   wherein the diaphragm is set to have a size such that a projection region by the diaphragm through the image-forming optical member on the photodetector overlaps the optical axis only within a predetermined amount, and such that the reflection light forms the image within the projection region by the diaphragm in projecting the measurement light onto a myopic eye with the measurable highest diopter.

2. The eye refractive power measurement apparatus according to claim 1, further comprising a movement unit which moves the optical system from the diaphragm to the photodetector in accordance with a refractive error of the eye to arrange the diaphragm and the photodetector at positions conjugate with the fundus.

3. An eye refractive power measurement apparatus for measuring eye refractive power of an eye of an examinee, the apparatus comprising:
   a measurement optical system including
      a projection optical system having a light source, which projects spot-shaped measurement light onto a fundus of the eye, and
      a photo-receiving optical system having
         an optical axis,
         a photodetector arranged on the optical axis,
         at least three apertures arranged at positions conjugate with a pupil of the eye, which are provided in at least three meridian directions on the same circumference having the optical axis as its center, and pass the light reflected from the fundus via a peripheral pupillary portion of the eye,
         an image-forming optical member arranged on the optical axis, by which the reflection light from the fundus via the peripheral pupillary portion and the respective apertures is deflected in directions away from the optical axis, and forms dot-shaped images on the photodetector, and a diaphragm having the optical axis as its center, which is arranged at a position conjugate with the fundus and on a side of the eye relative to the image-forming optical member; and
a calculation part which obtains the eye refractive power based on an output from the photodetector,
wherein the diaphragm is set to have a size such that projection regions by the diaphragm through the image-forming optical member on the photodetector are prevented from overlapping each other, and such that the reflection light forms the images within the projection regions by the diaphragm in projecting the measurement light onto a myopic eye with the measurable highest diopter.

4. The eye refractive power measurement apparatus according to claim 3, further comprising a movement unit which moves the optical system from the diaphragm to the photodetector in accordance with a refractive error of the eye to arrange the diaphragm and the photodetector in positions conjugate with the fundus.

* * * * *